United States Patent [19]

Carter et al.

[11] Patent Number: 5,035,508

[45] Date of Patent: Jul. 30, 1991

[54] LIGHT ABSORPTION ANALYSER

[75] Inventors: Timothy J. N. Carter, Sheppey; Roger A. Bunce, Bournville, both of England

[73] Assignee: National Research Development Corporation, London, England

[21] Appl. No.: 139,181

[22] Filed: Dec. 29, 1987

[30] Foreign Application Priority Data

Jan. 5, 1987 [GB] United Kingdom ............... 8700061

[51] Int. Cl.$^5$ .............................................. G01J 3/51
[52] U.S. Cl. ................................................... 356/416
[58] Field of Search ....................... 356/433, 409–411, 356/414, 416, 419, 432, 436, 440

[56] References Cited

U.S. PATENT DOCUMENTS

| 2,559,688 | 7/1951 | Touvet . | |
|---|---|---|---|
| 3,164,663 | 1/1965 | Gale | 356/436 |
| 3,810,696 | 5/1984 | Hutchin, Jr. | 356/435 |
| 3,958,852 | 5/1976 | Gast | 356/432 |
| 3,994,590 | 4/1976 | Di Martini et al. | 356/434 |
| 4,022,534 | 5/1977 | Kishner | 356/210 |
| 4,076,421 | 2/1978 | Kishner | 356/210 |
| 4,133,873 | 1/1979 | Noller . | |
| 4,241,998 | 12/1980 | Farkas et al. | 356/319 |
| 4,375,919 | 3/1983 | Busch | 356/328 |
| 4,419,583 | 12/1983 | Noller . | |
| 4,451,149 | 5/1984 | Noller . | |
| 4,561,779 | 12/1985 | Nagamuen et al. | 356/440 |
| 4,591,266 | 5/1986 | Doyle | 356/440 |
| 4,696,570 | 9/1987 | Joliot et al. | 356/319 |

FOREIGN PATENT DOCUMENTS

| 0081702 | 6/1983 | European Pat. Off. | 356/416 |
|---|---|---|---|
| 1959612 | 6/1971 | Fed. Rep. of Germany | 356/432 |
| 3026077 | 6/1982 | Fed. Rep. of Germany . | |
| 3332986 | 4/1985 | Fed. Rep. of Germany | 356/416 |
| 2088580 | 6/1982 | United Kingdom . | |

OTHER PUBLICATIONS

Williams et al. (1953), Journal of the Optical Society of America 43(7):595–599.
Greyson (1981), Journal of Automatic Chemistry 3(2):66–71.
Zipp (1981), Journal of Automatic Chemistry 3(2):71–75.
Von Paul Kubelka et al. (1931), Zeitschrift f. tech. Physik., 593–601.

Primary Examiner—Richard A. Rosenberger
Attorney, Agent, or Firm—Irell & Manella

[57] ABSTRACT

A light absorption analyzer can work in either a reflection or a transmission mode, according to which probe head is fitted to it.

Light is caused to be of a desired wavelength for the analysis by passing non-monochromatic light from a high-intensity flash tube source (which is not a point source) to an interference filter. Only parallel light emanating from the filter is focused by a concave parabolic mirror on a point where at least one fibre-optic collector is positioned. This light can then be passed directly to the probe for passage through the sample, since it is only light of a specified wavelength which will have travelled parallel from the filter and will therefore be focused at the point. Some of the light is taken off a reference detector to provide a reference signal for comparison with that derived from a test detetor fed by a return fibre-optic from the probe. A comparator is programmed to give a quantitiative readout of the absorption by the test sample.

10 Claims, 4 Drawing Sheets

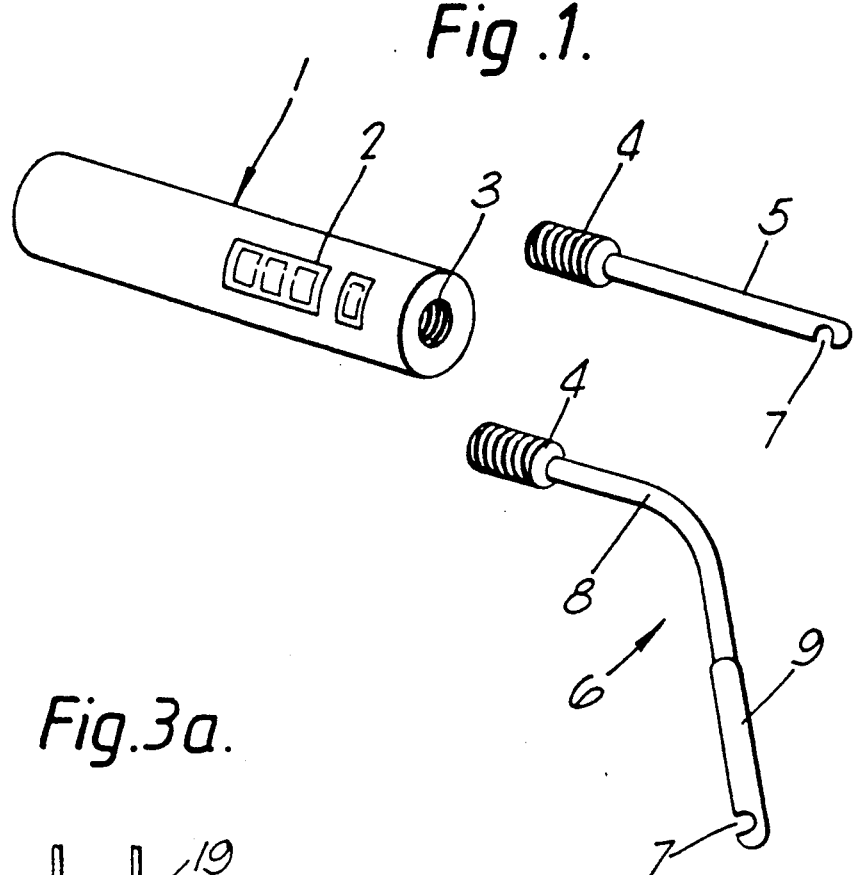
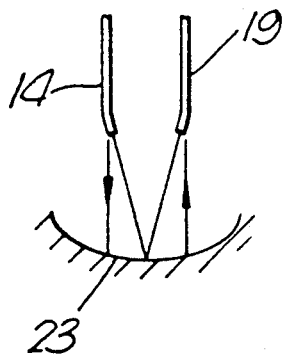
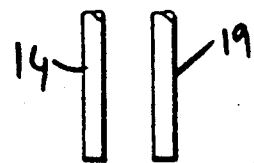
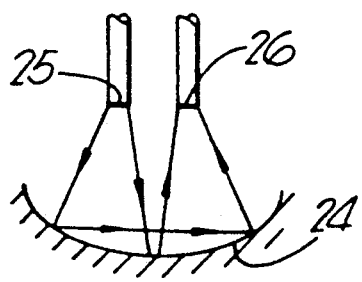
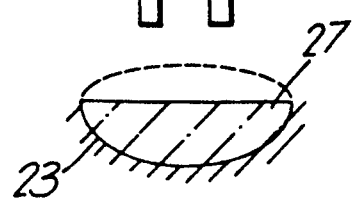

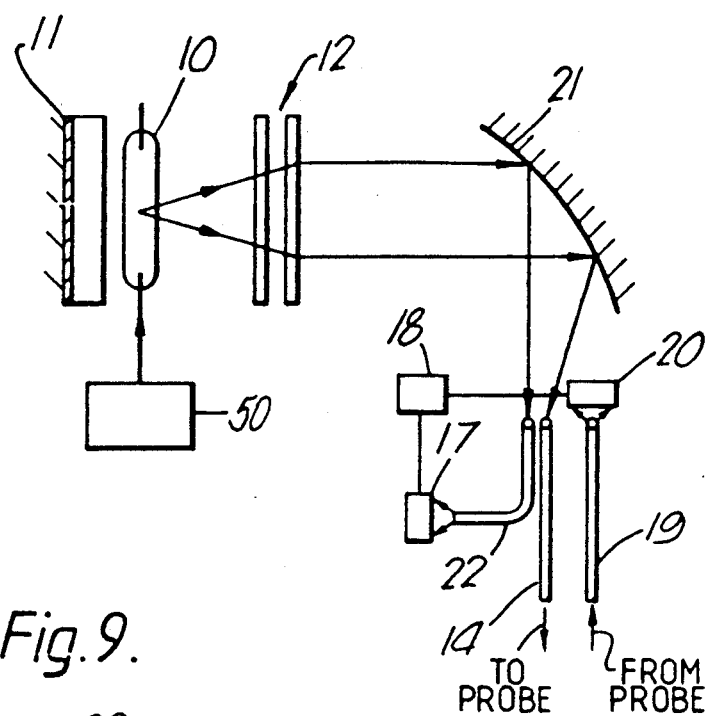
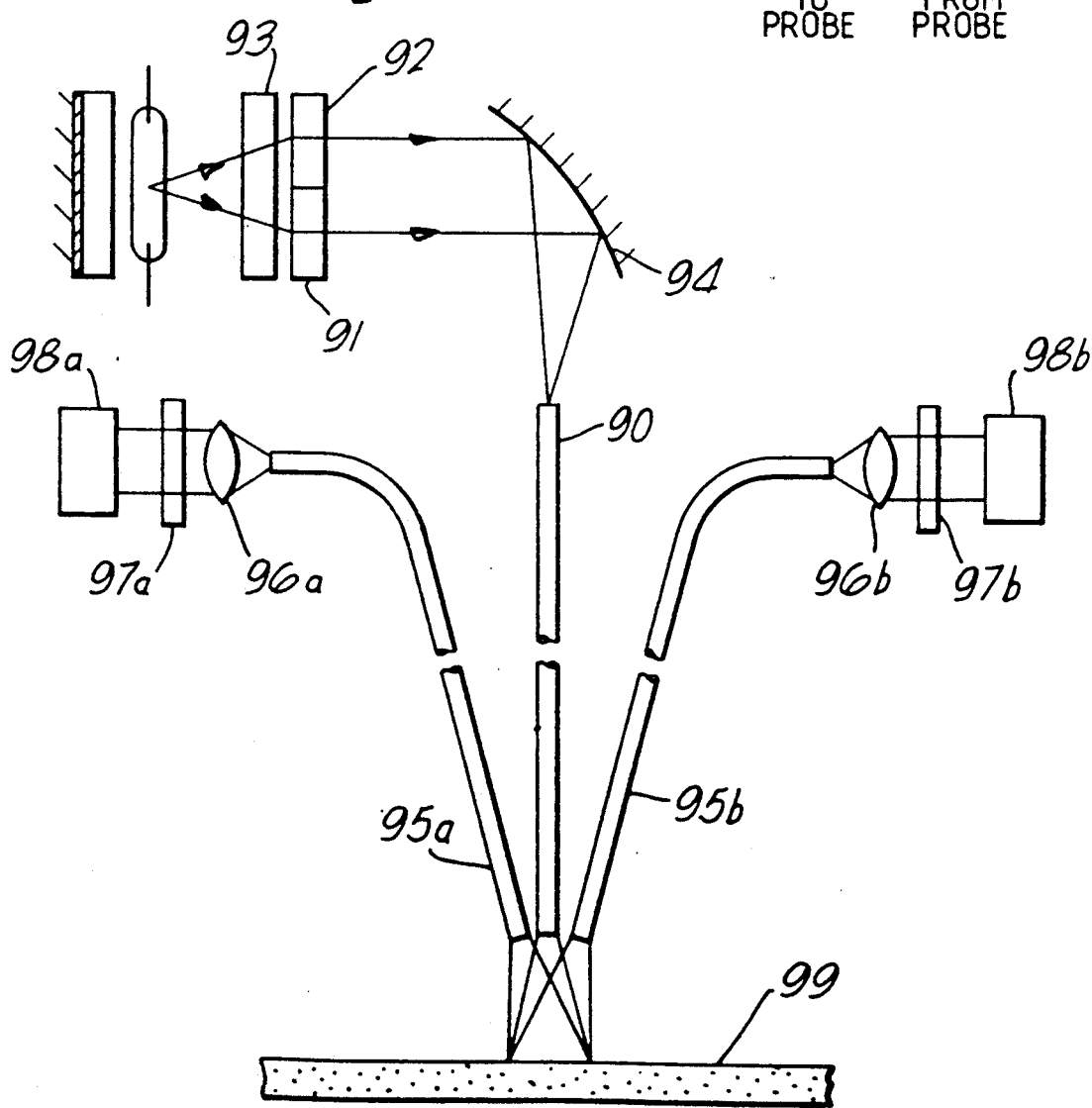

LIGHT ABSORPTION ANALYSER

This invention relates to light analysers. These measure light absorption at one or more specific frequencies either in transmission or reflection.

Traditionally these, most commonly represented by colorimeters, have been comparatively bulky, expensive and non-portable pieces of equipment.

The present invention is concerned to overcome several problems which have so far prevented these machines being produced in portable and widely usable form.

The present invention provides an analyser which can be portable and hand-held. It has a light emitting portion which emits pulsed light via a spectrophotometric arrangement towards a probe.

Such arrangements have been seen in the prior art.

In U.S. Pat. No. A 3810696, for example, the light source is a Xenon flash tube the output of which, assumed to be from a point-source, is passed through an interference filter. A collimator lens then renders the light parallel and part of it is passed through a sample, another part being used as a reference signal.

In U.S. Pat. No. A 4241998 ingenuity is exercised to make a Xenon flash tube appear to be a point source. The inventor had realized that such a tube is not a point source nor, at least in some types, is the origin of the discharge always located in the same place. To remedy that, output from a flash was focused by a lens onto one end of an integrating tube which randomized the light in such a way that by the time it emerged from the output end it could be considered as being from a single, precisely located, source. It could then be accurately handled by a grating monochromator. U.S. Pat. No. A 2559688 also tackles the problem of producing a "point source" from an extended Xenon tube source by the use of a special distorting optical system, which is a lens of considerable complexity.

Examples of monochromatization after absorption in a reflection mode are seen in U.S. Pat. No. A 4022534 and 4076421 which also use fibre optics as conductors, and similar principles are used in some Minolta "Chroma" reflectance meters. The main interest in the patents is in a head for providing light output to a test sample at 45° to the optical axis while receiving reflected input from the sample along that axis (the so-called "45/0" test), the source of light being a—non-point origin—Xenon flash tube. In a Minolta Chroma CR131 light is conducted to and from a reflectance sample by fibre-optics, again to achieve the 45/0 geometry. Monochromatization after coupling is also seen in FIG. 3 of Zipp, Journal of Automatic Chemistry (1981) 3, 2, p 71-75. This is a commercially available instrument known as a Seralyzer.

Another approach is to use a light source which is itself effectively monochromatic. It is seen in a commercially available instrument called a Reflotron which uses three LED's. However this is a restrictive approach and because of the comparatively low intensity of emission requires the use of an integrating sphere to maximise light collection. (The integrating sphere, which was first described in 1892, is used also in the Seralyzer and other known instruments).

Finally, Noller has proposed analysis systems using flash light sources for nephelometric assays (DE-A-3026077 and GB-A-208-858-0) and for fluoroimmunoassays (U.S. Pat. No. A 4133873, U.S. Pat. No. A 4419583, U.S. Pat. No. A 4451149).

In the present invention, we use a flash tube as the light source. Xenon tubes are very readily available, are reliable, have good efficiency and have a relatively even output over a wavelength range of 100–1000 nm.

A flash tube is not a point source. Whether it is the simple, very cheap, photographic flash tube or a more complex and expensive type such as that used in U.S. Pat. No. A 4241998 light is generated in random directions and from an extended origin. Obtaining light of only predetermined wavelength(s) from such a source has always in the past required the elaborate and often ingenious measures seen in the prior art.

The present invention achieves essentially light of a known wavelength by using a spectrophotometric arrangement which causes the light from the flash tube to act on an optical device of which the characteristic is to produce light of that wavelength in a single direction only, that is to say in a single angular direction in relation to the device. An interference filter is the most appropriate example; a diffraction grating is another.

No attempt need be made to align, focus or direct the light incident on the optical device, since the assembly includes a parabolic mirror placed in such a position in relation to the device that only parallel rays incident on the parabolic mirror from a single direction will be focused on a point; and at that point we place at least one collector. When we use the term "point" we use it in the sense usual in optics namely to mean a small area, and not in the strict geometrical sense. The collector may be any suitable optical system, but preferably a fibre-optic. Because only parallel rays will be focused at that point, only rays of the known wavelength emanating from the optical device will be collected. It does not matter that rays of other wavelengths may be passed by the device in other directions since these, if received by the mirror at all, will not be focused at the collecting point.

The collected light is then used in the desired analysis.

The extreme simplicity of the means for providing light of essentially only a known wavelength from a source which may be very cheap and easily powered, allows the present invention to overcome the problems of complexity, bulk and expense which have characterized the prior art.

Because the use of lenses may be entirely avoided, there is no restriction in the output wavelength(s) which may be selected for the spectrophotometric system.

The present analysers can be used for any kind of light assay; in transmission or diffuse reflection, including fluorimetry in either mode.

For operation in transmission, the collected light is led to a head of the probe which in use is dipped in the sample to be tested. After transmission through the sample being tested a signal is returned to the body of the analyser, where a comparison is made between the intensities of the output and return signals and converted into a display representing a ratio at the frequency selected by the spectrophotometric assembly. The signal may be returned after reflection at a mirror (preferably a concave mirror focusing the return signal onto a receiving collector of a return fibre optic) or after diffusion at a diffuse surface.

In reflection, the collector fibre-optic leads to a probe head in which the optic terminates in an emitter portion at a known distance from and at a known angle to, a test surface when in contact with the head. A receiving collector is also fixed in the head, to return a signal to the body of the analyser for comparison. The angles of the emitter portion and the receiving collector may be equal or may be in the 45/0 conformation; in either case the cone angles of the two will substantially overlap on the test surface.

Positioning of the test surface may be assured by a surface of the head; this may either offer discontinuous contact with the test surface, with an air gap between the ends of the fibre optics and the test surface, or be continuous, preferably with a diffusion surface on the head. Indeed the head may be solid with one of its faces acting as a diffusion surface and being for contacting the test surface.

The probe may project rigidly from the body or may be linked to it by a flexible lead containing one or more optical fibre conductors (output and return); the analyser may be provided with both a rigid and a flexible probe alternatively able to be fitted to the body containing the spectrophotometric assembly and the comparison and read out assembly.

Alternatively both output and return signals may be transmitted to and from the head of the probe using the same optical lead and suitable beam-splitting arrangements.

The optical device may be one arranged to cause two (or more) specified wavelengths only to progress in the predetermined direction. That is, there may be two interference filters arranged coplanar side by side so that the light collected consists of two wavelengths. Then, there may be a further reception collector in the head and/or the comparison circuitry may distinguish between responses at the two wavelengths. In this way, readings can be performed in a bichromatic mode (whereby interfering reactions are automatically accounted for), or can be obtained of changing systems e.g. in vivo oximetry readings.

Although the analyser may be powered from the mains through a transformer it is preferred to have it portably self contained by including a primary battery or batteries in a body of the analyser.

The flash tube produces an extremely high intensity of light, effectively swamping all but the highest daylight levels; and the pulse of light is short (of the order of milliseconds) and discrete, allowing it to be readily distinguished from the continuous and relatively invariable background daylight by suitable electronic means known to those skilled in the art. Therefore the sample may be tested, at least in transmission, without taking precautions for excluding daylight; in reflection however, such precautions may be necessary since considerably less light is reflected back. Such precautions may be readily taken by coating, e.g. painting, the probe head since in some cases "interference" might be experienced from light emanating from ordinary room-lighting fluorescent tubes.

An interference filter may be permanently built into the analyser or there may be a facility for exchanging the interference filter with one or more other interference filters to give a different selected range of wavelengths for the sampling. Similarly, a filter may be needed to eliminate infra-red and may be integral with or separate from the interference filter.

The electronic comparison circuitry may be arranged so as to respond to different ranges of sensitivity and so as to respond to the different responses as between transmission and reflection modes.

Applications of the analyser are found in chemical analysers and in in vitro diagnostic testing; and also in in vivo diagnosis where the probe may be applied continuously or otherwise to the patient. Examples of this last use are in testing for bilirubin levels and for anaemia.

Particular embodiments of the invention will now be described with reference to the accompanying drawings wherein:

FIG. 1 is a general view of the embodiment, with alternative probes;

FIG. 2 shows one spectrophotometric arrangement;

FIGS. 3a, 3b and 3c show optical arrangements of a probe;

FIG. 9 shows a modification in which reflection is measured at two different wavelengths.

Figure 4:
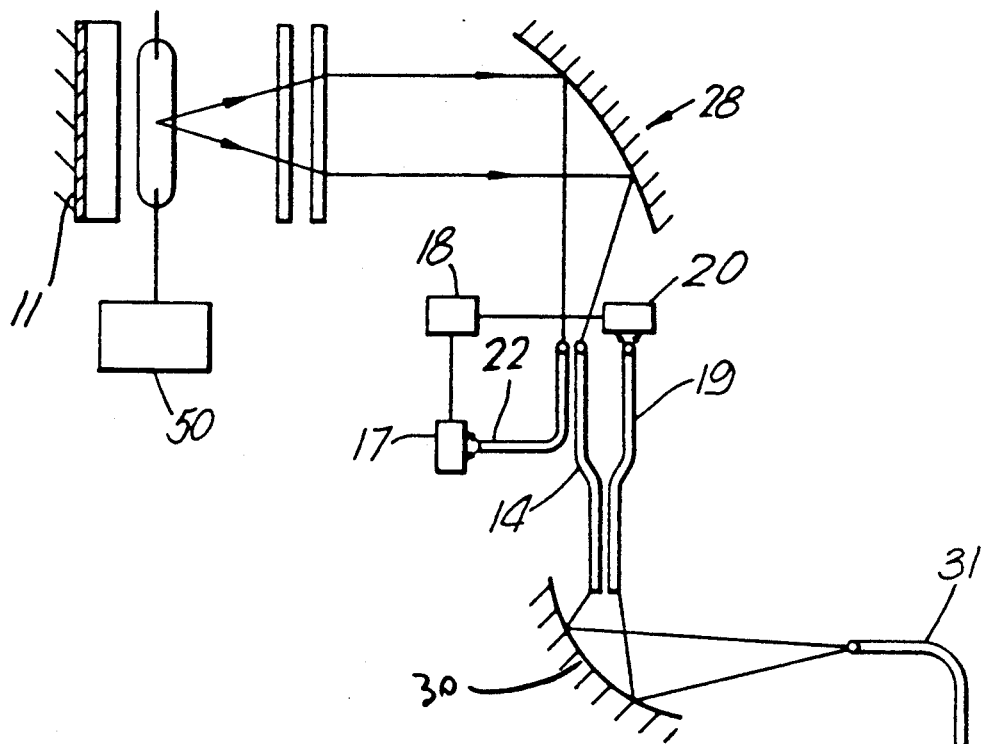
FIGS. 4 and 5 show alternative transmission arrangements.

In FIG. 1, a hand-holdable body 1 encloses the working parts to be described. A window 2 allows the user to see a display panel. A socket 3 is for the reception of jacks 4 of alternative probes 5, 6. The probe 5 is a rigid tube which when fitted is a continuation of the body 1 and a window 7 in its end is inserted in a liquid to be tested by appropriate manipulation of the body. The probe 6 is flexible, with a duct 8 leading to a tip 9 with a window 7. This obviously renders the position of the probe independent, within limits, of the position or attitude of the body 1. Of course, either probe arrangement can be made permanently attached to the body 1.

The optical system within the body may be one of those to be described.

FIG. 2 shows a pulsed source of light as a high intensity Xenon flash tube 10 excited from a power supply 50. Light from the tube passe through filters the first of which is a thermal (infrared) filter 12 and the second of which is interference filter 13. Partcylindrical reflector 11 reflects light towards the filters. A characteristic of interference filters is that light of the desired frequency is passed (for the present purposes) only normal to the plane of the filter. A doubly parabolically concave mirror 21 focuses only that light which has passed normal to the plane of the filter 13 onto a point where there is a light collector; in this case into the inlet end of a fibre-optic conductor 14 leading to the probe 5 or 6 and also onto the inlet end of a fibre-optic conductor 22 leading to a comparison detector 17. The cone angle of the focused beam should approximately match or be within the collection cone angle of the fibre-optic. To prevent internal reflection the interior of the body should be strongly light-absorbent being e.g. matt black or being lined with black optical felt.

Other arrangements are possible for taking off part of the beam to a comparison or reference detector. One example is a beam splitter. Furthermore, especially if fluorimetry is being performed, the reference beam may be taken off before monochromatisation. The reference detector 17 is preferably a solid state detector such as a silicon photodiode. Its electrical output is taken to an electronic comparator 18.

Light returned from the probe via fibre-optic 19 is fed to a "test" detector 20, also preferably solid-state and matched to detector 17, whose output is also taken to the comparator 18.

Various optical arrangements of the probe head are seen in FIG. 3. Light from an output end of the fibre-optic 14 (or where the probe assembly is detachable from the body 1, from a fibre optic aligned with fibre-optic 14 by the socket and jack arrangement) is projected towards a concave mirror 23 which will be housed in the extreme end of the probe beyond the window 7. It reflects light accurately to the input end of the return fibre-optic 19 (or in the case of the detachable probe assembly the input end of a fibre-optic aligned with fibre-optic 19).

If a paraboloid or spherical mirror 23 is used in the probe head, the ends of the fibre optics 14, 19 are placed approximately at twice the focal length of the mirror, but are inclined slightly towards each other to look at the same area of the mirror. If the mirror is ellipsoidal as at 24 in FIG. 3b, the ends of the fibre optics ar placed respectively at the two foci 25, 26 of the mirror.

As shown in FIG. 3c the concavity of the mirror may be filled with a transparent material 27 with a flat or concave surface to prevent lodging of possibly corrosive or interfering material in the mirror; alternatively a non-corrodable material should be used as the mirror surface.

A further modification replaces the mirror by a flat diffusion plate. The system will then be working effectively in a diffuse reflectometry mode, as will be explained.

Figure 5:
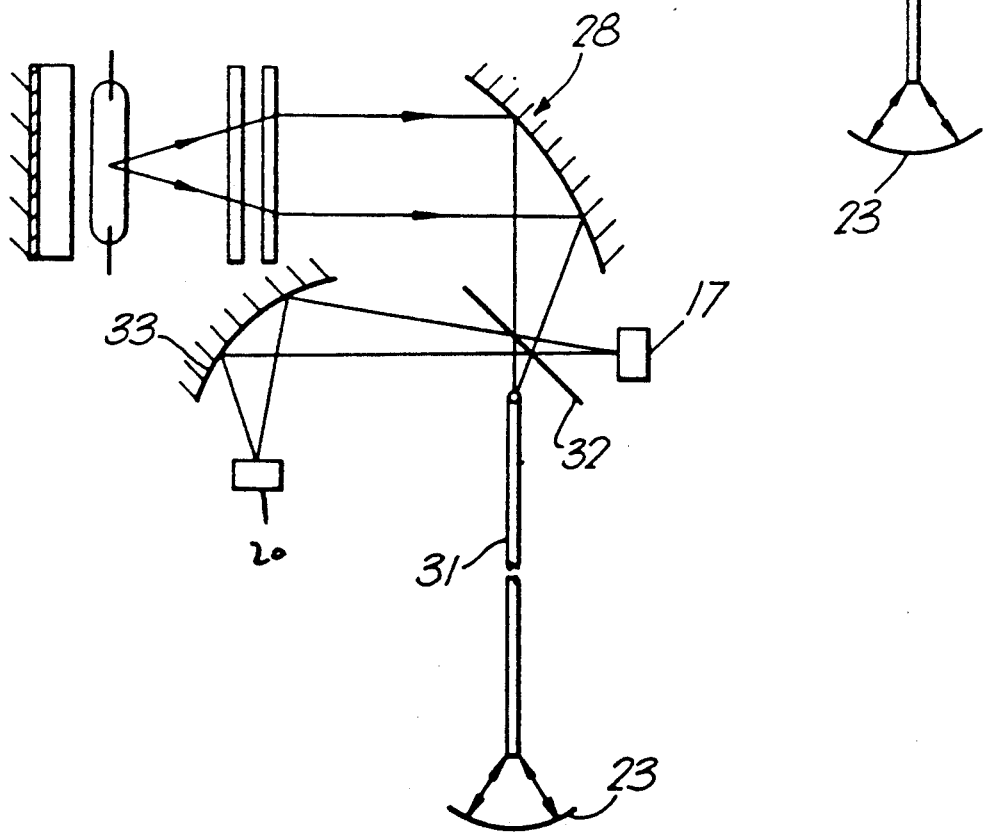

FIGS. 4 and 5 show how a single optical lead may go to the head of the probe.

In FIG. 4 an optical system as in FIG. 2, here given a general reference 28, feeds an input fibre-optic 14 and a reference detector 17, the latter via fibre-optic lead 22.

A beam from the fibre-optic lead 14 is reflected from a spherical concave mirror 30 onto a single fibre-optic lead 31 going to a head of a probe and ending at the focal point of a mirror 23. The beam returning via the lead 31 is picked up by output lead 19 and directed to a test detector 20 as before.

FIG. 5 shows an optically less efficient way of achieving the same end A planar half-mirror 32 reflects a) the input beam to the reference detector 17 and b) the return beam from the single lead 31 to the test detector 20 via a focusing mirror 33.

Referring to FIG. 2, in use the probe end is dipped in the liquid to be tested. The liquid enters through the window 7. Light from the source 10 filtered to a desired frequency passes from the fibre-optic 14 to the mirror or the diffusion plate and back to the fibre-optic 19, with therefore a double passage through the liquid.

The difference between output and input intensities is measured by the comparator 18 which is arranged to give a reading on the display 2. The comparator 18 also detects only signals due to the pulsed source 10, eliminating "noise" due to ambient light. Since the Xenon discharge is of very high intensity this latter effect is anyway marginal.

If desired the body may be arranged to give access to the filters 12 and 13 so they may be exchanged for other(s) of different frequency. Alternatively a variable monochromator such as a grating, prism or interference wedge may be submitted for the interference filter 13 to give the opportunity of scanning over a range of wavelengths by adjustment of its setting.

The signals being processed are short pulses of high intensity. They could be assessed either in peak values, on some intermediate value or on integrated values. We prefer to assess the signals using integrated values as they give more precise results. Further precision may be obtained by arranging that a test involves an automated burst of a number of pulses, say ten, the mean of the integrals of which is taken as the reading.

It is useful that the readings from the analyser are presented on the same numerical scales as are customary for standard path-lengths, e.g. 1 cm cell, colorimeters. To achieve this, the following conversions may be programmed into the present analyser.

Let $Ds$ = solvent signal from the test detector (i.e. the signal obtained when at the start of a run the probe is dipped into the solvent to be used)

$Dr$ = Reference signal (i.e. the signal from the reference detector)

$Dt$ = Test signal (i.e. the signal from the test detector when in the solution to be analysed)

$T$ = Transmission $b1$ = standard path-length (in this example 1 cm)

$b2$ = equivalent path length of probe $A$ = Absorbence $$\frac{Ds}{Dr} = \text{constant } K$$

By definition $T = \frac{Dt}{Ds} \therefore T = \frac{Dt}{K \cdot Dr}$ (1)

Let $\frac{b1}{b2} = F$

For a 1 cm path length, by definition $A = \log_{10} \frac{1}{T}$ (2)

Substitute 1 into 2 $A = \log_{10}(\frac{K \cdot Dr}{Dt})$

And since $A$ path length $A = F \log_{10}(\frac{K \cdot Dr}{Dt})$

In effect K is a constant (at a given time) for the solvent used and F is a constant for the probe used, both at a given wavelength. Calibration for F is to be obtained by use of a sample of known absorption (which may be a filter rather than a known solution).

Since F is then known and K is obtained at the beginning of each test run, A may be calculated.

Alternatively, replacement probes may be calibrated in the factory always to have the same value of F e.g. by the insertion of ratisable filters or obstructors.

In a further embodiment, the analyser is used to determine fluorescence. The pulse excites a fluorescent solution at its known wavelength. Fluorescence at a longer wavelength may be detected by the test detector provided that an appropriate filter is fitted between it and the return probe to exclude light of the excitation wavelength.

The analyser can also be used to detect light-scattering, by reflection from the test sample without the use of a mirror, or as an optrode i.e. with the end of the lead coated with a chemical such as an enzyme for fluorimetric immunological analysis, for example.

Furthermore, by arranging suitable "time sharing" optics a plurality of probes may be fitted to and be serviced from a single body and be used simultaneously to examine different samples.

Figure 6:
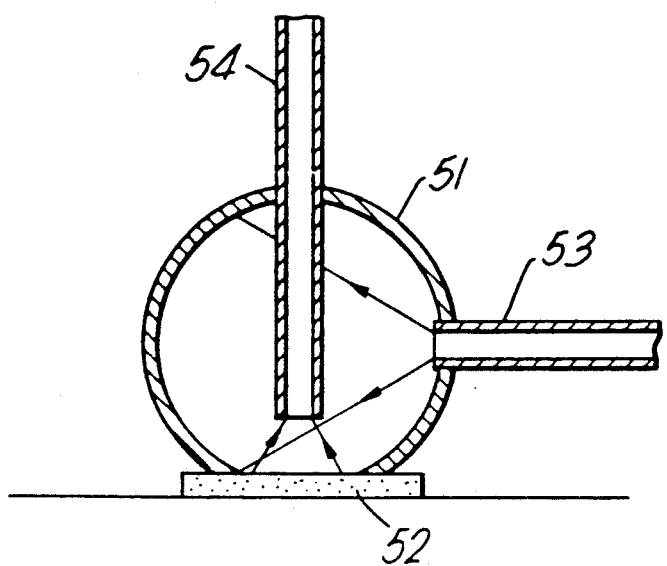
FIG. 6 shows a section through an integrating sphere fitted to the two fibre optics in place of the mirror assembly described previously.
Figure 7:
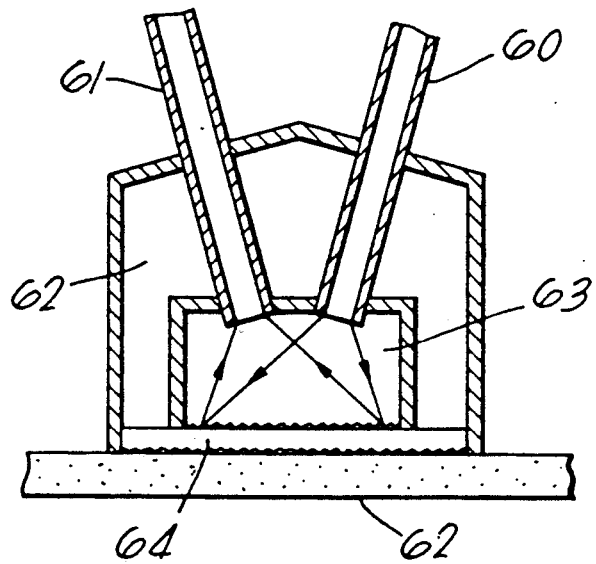
FIG. 7 shows a section through a first reflective probe.
Figure 8:
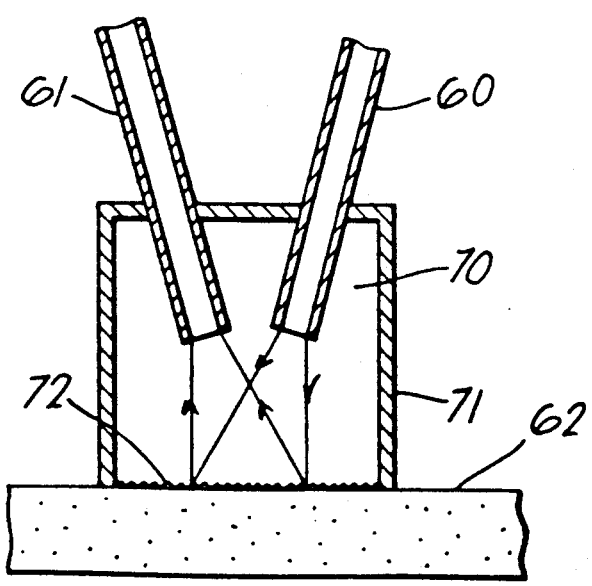
FIG. 8 shows a section through a second reflective probe.

In the reflection mode, the light from the spectrophotometric arrangement is led to a probe head as described for example in FIGS. 6–8.

In the first of these, seen in FIG. 6, an integrating sphere of small dimension can be used in the head.

The integrating sphere 51 is internally coated with white diffuse paint in the normal way and serves to evenly illuminate the specimen contained in absorbent pad 52. The integrating sphere is fed with light from fibre optic 53 from the optical system described previously. Fibre optic 53 is positioned such that direct light from it does not enter fibre optic 54 which is positioned so that it gathers only the light which is diffusely reflected from the specimen pad 52.

FIG. 7 shows an illuminating fibre optic 60, and a receiving fibre optic 61. The fibre optics are positioned and angled such that the illuminating area and receiving area of light substantially coincide at the specimen pad. It is emphasised that although the fibre optics are shown symmetrical this may not always be so and, for example, one fibre optic could be positioned normal to the specimen pad surface and the other at 45 degrees to the surface. The fibre optics are fitted into a block 62 which ensures the correct spacing and orientation to the specimen surface. The block is provided with cavity 63 to allow free passage of the acceptance cones of light of the fibre optics. The material of block 62 is substantially opaque. Although the optical system is immune to normal ambient daylight the "flickering" light from a fluorescent tube can cause interference. The reflectance probe can be placed directly on the surface of the specimen, or to prevent wetting of the probe, and to define the specimen surface to probe distance more accurately, a cover-slip may be interposed between probe and specimen surface 64. The cover-slip must be made from a translucent material such as plastic. The surfaces of the cover-slip are preferably made diffuse so as to minimise the effects of direct (specular) reflection and for obviate variations due to the nature of the test material carrying the specimen. The cover-slip could either form part of the probe or specimen unit, or be separate.

FIG. 8 shows a similar arrangement to FIG. 7, but in this case the fibre optics are encapsulated by a substantially transparent material such as a thermoplastic or polyester resin type material 70. The outer surface of the encapsulation is preferably covered in an opaque material such as black paint or resin 71. The lower surface 72 of the probe would preferably be optically diffuse, as described previously. This construction of probe has the advantage of being more easily decontaminated than that shown in FIG. 7.

The arrangement seen in FIG. 9 enables reflectance to be measured at two different wavelengths simultaneously. One wavelength is chosen to coincide with the maximum absorbance of the analyte and the other is a totally different wavelength. These two reflectances can be ratioed so that the system automatically compensates for pulse to pulse variation of the lamp and also for, so called, interfering substances in the analyte. The principle of two wavelength compensation is well known.

Fibre optic 90 may be supplied by light of the two appropriate wavelengths from two interference filters 91 and 92 interposed between the infrared blocking filter 93 and offset paraboloidal mirror 94. Fibre optic 90 "mixes" the two wavelengths and directs them onto the surface 99 of the specimen. Two more fibre optics 95a and 95b collect the diffusely reflected light from the sample surface and direct it, via collimating lenses 96a and 96b through interference filters 97a and 97b. These filters correspond in value to filters 92 and 91 and hence separate the two component wavelengths. Optical detectors 98a and 98b convert the light to a proportional electrical signal. These signals are fed to a microcomputer for computation of the analyte contained in the specimens.

It will be realized that the two collimating lenses 97a and 97b can be replaced by mirrors as used elsewhere in the system.

There have been at least two theoretical models for reflectometry in the past: the Kubelka Munk formula (Zeitschrift fur technische Physik, 1931, 11a, p 593–601) and the Williams-Clapper relationship (J. Opt. Soc. America, (1953) 43, 7, p 595–599). The first investigates the relationship between a diffuse substrate, its thickness and the material absorbed therein: the second the redistribution of illumination in a multiple-layer substrate, assuming a 45° angle of incidence. In practice, the derivation conditions of the theoretical analyses are not met exactly, and the relationship of reflectance and absorbence (or analyte concentration) is derived empirically. This is particularly relevant in the case of complex molecules such as biological specimens, analysis of which usually involves comparison with a reference material of known composition.

Provided, therefore, that the sample specimen, such as a filter paper, has more than a minimal thickness and is adequately moistened with test liquid reproduceable and quantitative results may be obtained without reliance on previous reflectometric theory.

We claim:

1. A light absorption analyser comprising:
   a body
   a probe head
   a flash tube in said body and actuatable to emit output pulses of light
   spectrophotometric means in said body for receiving light from said flash tube,
   said spectrophotometric means including
      a) an interference filter for passing only light of a predetermined frequency in a given direction and
      b) a doubly concave parabolic mirror for receiving said light in said given direction and focusing said light to a point in said body, and
   collector means at said point, said collector means including at least one fibre-optic output light conductor,
   said light conductor being for conducting said collected light to said probe head from said body.

2. A light absorption analyser according to claim 1 further comprising
   fibre-optic light conductor means for returning light form said probe head to said body, and
   comparator means in the body for comparing said pulsed light with said returned light.

3. A light absorption analyser according to claim 2 wherein said probe head is adapted for transmission absorption and includes
   an output end of said output conductor
   an input end of said return conductor reflection means spaced from said ends at a distance whereat cone angles of the conductors overlap and window means for allowing access of fluid medium to be tested to be interposed between said ends on the one hand and said reflection means on the other hand.

4. A light absorption analyser according to claim 3 wherein said reflection means is specular.

5. A light absorption analyser according to claim 3 wherein said reflection means is a diffusion plate.

6. In a light absorption analyser for examining a sample by exposing said sample to light of a predetermined wavelength, the improved spectrophotometric arrangement comprising, in combination, a flash tube constituting an extended source of non-monochromatic light for radiating said non-monochromatic light in random directions, an optical device having an extended surface exposed to light form substantially the entire extended source, with said non-monochromatic light from different parts of said extended source being incident in a predetermined direction at correspondingly different points of said extended surface, said device for causing light of only a predetermined wavelength and incident of said extended surface only in said predetermined direction to proceed from said device in a given direction in space, and a parabolic mirror positioned to receive, and focus at a given position, the light of said predetermined wavelength proceeding from said optical device in said given direction, said light focused at said given position being for use in said examination.

7. The analyser as claimed in claim 6 wherein the said spectrophotometric arrangement is contained in a body of said analyser, said light from said position being collected by collector means and passed by output means to a probe head, return means passing light from said probe head to said body, means at said probe head to cause said examining light to impinge on the sample to be examined and for light from said sample to be returned by said returning means.

8. The analyser as claimed in claim 7 wherein said probe head is removably attached to said body and forms a rigid entity therewith.

9. The analyser as claimed in claim 7 wherein said probe head is removably attached to said body and is flexibly linked therewith.

10. The analyser as claimed in claim 7 wherein said head is a solid block of translucent material encapsulating said output and return means, a surface of said block being adapted to contact a solid said sample.

* * * * *